US010363050B2

(12) United States Patent
McGinley et al.

(10) Patent No.: US 10,363,050 B2
(45) Date of Patent: Jul. 30, 2019

(54) VARIABLE DIAMETER DRILL BIT GUIDE

(71) Applicant: McGinley Engineered Solutions, LLC, Casper, WY (US)

(72) Inventors: Joseph C. McGinley, Casper, WY (US); Vincent Palazzolo, Casper, WY (US); Ben Warren, Glenrock, WY (US); Adam M. Johnson, Casper, WY (US)

(73) Assignee: McGinley Engineered Solutions, LLC, Casper, WY (US)

( * ) Notice: Subject to any disclaimer, the term of this patent is extended or adjusted under 35 U.S.C. 154(b) by 189 days.

(21) Appl. No.: 15/335,080

(22) Filed: Oct. 26, 2016

(65) Prior Publication Data

US 2017/0189037 A1    Jul. 6, 2017

Related U.S. Application Data

(60) Provisional application No. 62/247,019, filed on Oct. 27, 2015.

(51) Int. Cl.
*A61B 17/17* (2006.01)
*A61B 17/16* (2006.01)

(52) U.S. Cl.
CPC .......... *A61B 17/17* (2013.01); *A61B 17/1617* (2013.01)

(58) Field of Classification Search
CPC ............................ A61B 17/17; A61B 17/1617
USPC .............. 606/96–98; 81/13, 456; 408/115 R, 408/241 G
See application file for complete search history.

(56) References Cited

U.S. PATENT DOCUMENTS

| 437,796 | A | * | 10/1890 | Preston | B23B 47/28 |
| | | | | | 408/72 R |
| 907,735 | A | * | 12/1908 | Cain, Jr. | B23B 47/28 |
| | | | | | 33/555.2 |
| 3,171,408 | A | * | 3/1965 | Childs | A61B 17/17 |
| | | | | | 606/96 |
| 3,704,707 | A | * | 12/1972 | Halloran | A61B 17/1703 |
| | | | | | 378/162 |
| 3,775,020 | A | * | 11/1973 | Stoutenberg | B23B 49/02 |
| | | | | | 408/115 R |
| 3,804,546 | A | * | 4/1974 | Boyajian | B23B 49/02 |
| | | | | | 408/115 R |
| 4,788,970 | A | * | 12/1988 | Karas | A61B 17/1728 |
| | | | | | 606/80 |

(Continued)

FOREIGN PATENT DOCUMENTS

WO    WO 2017075060 A1 *    5/2017  ............. A61B 17/15

*Primary Examiner* — Kevin T Truong
*Assistant Examiner* — Jessica Weiss
(74) *Attorney, Agent, or Firm* — Holzer Patel Drennan

(57) ABSTRACT

Drill bit guide assemblies related to surgical operations for guiding and stabilizing a drill bit. A guide member houses a fixed bore through which a drill bit may pass. The guide member may also house a bore selection member which houses a plurality of selectable bores. The selectable bores may have a variety of diameters such that a user may choose the selectable bore corresponding to the drill bit diameter being used and align that selectable bore with the fixed bore such that the drill bit may pass through the length of the assembly along the reference axis. The similar diameters of the selectable bore and the drill bit may cause the assembly to stabilize and guide the drill bit.

18 Claims, 19 Drawing Sheets

(56) References Cited

U.S. PATENT DOCUMENTS

| | | | | |
|---|---|---|---|---|
| 5,415,502 | A | * | 5/1995 | Dahlin .................... B23B 47/28 |
| | | | | 408/115 B |
| 5,445,641 | A | * | 8/1995 | Frigg ................. A61B 17/1735 |
| | | | | 221/113 |
| 5,743,916 | A | * | 4/1998 | Greenberg ............. A61B 17/02 |
| | | | | 606/102 |
| 5,888,034 | A | * | 3/1999 | Greenberg ............. A61B 17/02 |
| | | | | 408/115 R |
| D533,571 | S | * | 12/2006 | Degen .......................... D15/140 |
| D791,944 | S | * | 7/2017 | Palazzolo .................... D24/140 |
| 2002/0170840 | A1 | * | 11/2002 | Happonen ............ A61B 17/105 |
| | | | | 206/338 |
| 2009/0311058 | A1 | * | 12/2009 | Canas Fontan .... B23Q 11/0053 |
| | | | | 408/115 R |
| 2013/0023881 | A1 | * | 1/2013 | Cook .................... A61B 17/17 |
| | | | | 606/80 |

\* cited by examiner

VARIABLE DIAMETER DRILL BIT GUIDE

RELATED APPLICATIONS

This application claims the benefit of U.S. Provisional Patent Application No. 62/247,019 filed Oct. 27, 2015, entitled "VARIABLE DIAMETER DRILL BIT GUIDE," which is incorporated herein by reference in its entirety.

FIELD

The present disclosure relates to instruments for assistance in surgery, and in particular to guides for assisting in guiding an instrument when performing an operation.

BACKGROUND

Orthopedic procedures may require precise alignment of a surgical instrument in relation to a surgical site. Slippage and/or incorrect positioning of the surgical instrument may result in damage to a patient. This may lead to surgical complications, which are undesirable. For instance, tissue may be exposed and potentially subjected to infection. Furthermore, improper surgical instrument alignment may result in increased operating time and cost, increased recovery time and pain, as well as reduce the effectiveness of the procedure.

Prior approaches have been contemplated that include drill bit guides comprising a shaft or a handle with a bore on one end or in some instances, on both ends. The location and size of the bore relative to the shaft or handle is fixed. Accordingly, when a surgeon requires use of multiple drill bits, each with a different diameter during a single procedure, the surgeon will require a corresponding plurality of drill bit guides. Such a plurality may occupy a significant amount of space in an operating room wherein there is little room to spare. Additionally, a surgeon and his/her staff may misplace a single drill bit guide from the plurality resulting in delays during the procedure and potentially use of a drill bit guide which is not properly sized for the needed drill bit. Furthermore, there is an added cost when a plurality of drill bit guides are needed.

SUMMARY

The present disclosure relates generally to systems, methods, and apparatuses for use with a surgical instrument, such as a drill, saw, reamer, grinder, or the like. More specifically, the present disclosure presents embodiments related to a system for aligning an instrument with a desired location by using a tool guide assembly. For example, the tool guide may comprise a drill bit guide comprising multiple selectable bores with various diameters. As such, in at least some embodiments herein, a drill bit guide assembly is described where a user may choose a specific diameter bore from a selection of bores with different diameters. Additionally, the present disclosure may include embodiments that contain multiple bore selection members which are engaged simultaneously. Accordingly, the present disclosure may find application in the field of surgical drilling where the penetration requires accuracy and precision.

The present disclosure also includes embodiments of drill bit guide assemblies that may be specifically adapted for use with an extension member. Accordingly, the drill bit guide assemblies disclosed herein may provide increased efficiency, reliability, and accuracy in relation to drill penetration in surgical applications. For instance, in certain embodiments, a drill bit guide assembly may be used in conjunction with a drill as described herein to provide an improved platform to facilitate precision of a bore created by a drill.

The disclosed embodiments provide a number of benefits over the prior art. For instance, a user can quickly switch between drill bit sizes without needing to swap drill bit guides. In a complicated or time sensitive surgical procedure, the time savings may be significant which reduces risk for the patient and improves the surgeon's efficiency. Furthermore, there may be cost savings that result from a decrease in the amount of raw materials needed to produce the disclosed embodiments versus the traditional plurality of drill bit guides. Furthermore, the guide may include an ergonomically provided handle that may make gripping and utilization of the guide more comfortable for the user. For instance, this handle may be integrally provided with the guide.

Accordingly, a first aspect includes a drill bit guide assembly for use with a drill having a plurality of selectable bores with various diameters for quickly adjusting to the changing of drill bits. The assembly includes a guide member, a fixed bore, and a bore selection member. The guide member may include a handle. The handle may be disposed at a proximal end of the drill bit guide assembly. Alternatively, the guide member may include a handle disposed between a distal end and a proximal end of the drill bit guide assembly. The guide member may include a fixed bore that is adapted for guiding a drill bit during operation. The central axis of the fixed bore may comprise a reference axis which may be desired as the target axis for penetration of the drill bit. The bore selection member may be comprised of at least one of a plurality of selectable bores which includes bores of various diameters. Each bore diameter may be designed to correspond to a standard drill bit diameter common in surgical practice.

A number of feature refinements and additional features are applicable to the first aspect. These feature refinements and additional features may be used individually or in any combination. As such, each of the following features that will be discussed may be, but are not required to be, used with any other feature or combination of features of the first aspect.

For example, in an embodiment, the bore selection member may comprise only a single selectable bore. In such an embodiment, a plurality of bore selection members may be provided that may be attachable and detachable (i.e., interchangeable) from the guide member as needed. The bore selection members corresponding to the diameter of the drill bit being utilized at the time may be attached at least one at a time and the detached members may be unused during such stage of the surgical operation until needed.

In an embodiment, the bore selection member may be affixed to the guide member for movement relative to the fixed bore. In such an embodiment, the bore selection member may be comprised of at least one selectable bore which may be alignable with the fixed bore to guide the drill bit.

In an embodiment, the bore selection member may comprise at least one selectable bore disposed at the outer perimeter of the bore selection member in such a manner as to create a gap in the perimeter surface of the bore selection member. In this regard, the surface of a selectable bore may not completely surround a drill bit but rather may only partially circumscribe a drill bit to substantially restrict movement to only the axial direction of the drill bit. In such an embodiment, a drill bit may be partially disposed on both sides of the perimeter surface.

In an embodiment, the bore selection member may be rotatable relative to the guide member to align a selectable bore with the fixed bore. In such an embodiment, the bore selection member comprises a distal surface and a proximal surface and a perimeter surface extending between the distal surface and the proximal surface. In this embodiment, the bore selection member may further comprise a plurality of bores, each of which extends from the proximal surface to the distal surface. In such an embodiment, one of the bores may be disposed about an axle wherein the axle is affixed to the guide member and is parallel to and is eccentrically disposed from the reference axis. In other embodiments, the axle may eccentrically disposed but not parallel to the reference axis.

In another embodiment, the bore selection member may be slidably moveable relative to the fixed bore. In such an embodiment, the bore selection member may comprise a plurality of selectable bores each of which may be aligned with the fixed bore to guide a drill bit.

In an embodiment, the drill bit guide assembly may include an index system. The index system may include a first indexing member fixed relative to the reference axis and a second indexing member fixed relative to the bore selection member. There may be additional indexing members, each of which correspond to a particular selectable bore. As the bore selection member is moved, the first indexing member cooperates with another indexing member to align the chosen selectable bore with the fixed bore. The first indexing member may be a locking pin and the second indexing member may be a locking cavity wherein the locking pin and locking cavity are of similar size. The bore selection member may be positioned such that the locking cavity is disposed about the locking pin, restricting movement of the bore selection member.

In an embodiment, the index system may further comprise a plurality of indicia wherein the indicia are each disposed relative to the plurality of selectable bores such that a given indicium denotes which selectable bore is currently aligned with the fixed bore.

In an embodiment, a distal end of the guide member may comprise an attaching mechanism which is engageable to an extension member. The attaching mechanism may include threads which are engageable to complementary threads on the extension member. The attaching mechanism may also be a friction or interference fitting wherein the extension member may be seated tightly against the guide member. In another alternative, the attaching mechanism may comprise a clip which latches or is otherwise securably engageable onto the extension member. There are any number of alternative attaching mechanisms, each of which are contemplated by the present invention.

The extension member may be of sufficient length to increase the overall length of the drill bit guide assembly thereby increasing stability of the drill bit used to access surgical sites (e.g., recessed sites). Alternatively, the extension member may simply serve to adjust the geometry of the distal end to affect interaction between the drill bit guide assembly and the surgical site.

In an embodiment, the drill bit guide assembly may comprise additional bore selection members. In one such example, the reference axis may pass through one or more guide members comprising the fixed bore as well as multiple bore selection members. Additional bore selection members or guide members may improve stability in guiding the drill bit.

DETAILED DESCRIPTION

Figure 1:
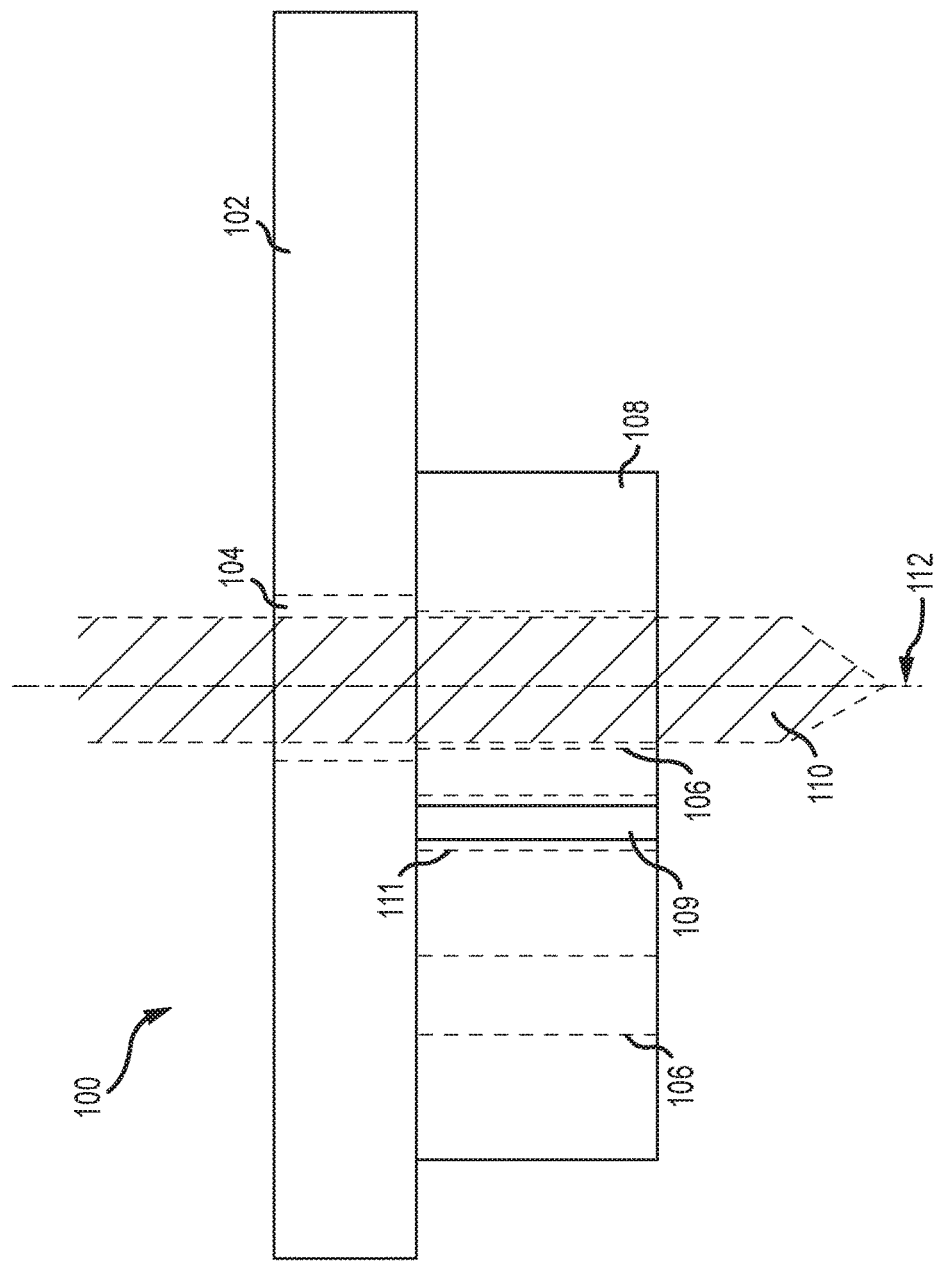
FIG. 1 is a schematic sectional view of an embodiment of a drill bit guide assembly featuring a rotational bore selection member.

The following description is not intended to limit the invention to the forms disclosed herein. Consequently, variations and modifications commensurate with the following teachings, skill and knowledge of the relevant art, are within the scope of the present invention. The embodiments described herein are further intended to explain known modes of practicing the invention and to enable others skilled in the art to utilize the invention in such, or other, embodiments and with various modifications required by the particular applications(s) or use(s) of the present invention.

Certain terminology is used in the following description for convenience only and is not limiting. The words "lower"

and "upper" designate directions in the drawings to which reference is made. As used in the claims and in the corresponding portion of the specification, the word "a" means "at least one". Further, unless otherwise defined the word "about" when used in conjunction with a numerical value means a range of values corresponding to the numerical value plus or minus ten percent of the numerical value. Still further, the word "or" has the meaning of a Boolean inclusive "Or". For example, the phrase "A or B" means "A" alone or "B" alone or both "A" and "B". In some drawings which contain a plurality of a certain element, less than all of the instances of that element have been labelled in order to avoid excessive labelling obstructing the figure itself. Furthermore, in some instances a single element is labelled in multiple locations within a single drawing to provide clarity.

Referring to the drawings in detail and in particular to FIG. 1, there is shown a first embodiment of the drill bit guide assembly generally designated 100. The drill bit guide assembly 100 includes a guide member 102. The guide member 102 is comprised of at least a portion of a fixed bore 104. The central axis of the fixed bore 104 defines a reference axis 112. Furthermore, the guide member 102 may include and/or provide a point of attachment for a handle (not shown in FIG. 1).

A bore selection member 108 is also provided in relation to the guide member 102. In this embodiment, the bore selection member 108 may be affixed to the drill bit guide assembly 100 in a manner in which the bore selection member 108 may rotate about an axle 109. The bore selection member 108 may contain a plurality of selectable bores 106 each of which may be alignable with the fixed bore 104 such that a drill bit 110 may pass through both the fixed bore 104 and a selectable bore 106 along the reference axis 112 (e.g., by rotation of the bore selection member 108 about the axle 109). The selectable bores 106 may have different diameters. A user may choose a selectable bore 106 that is similar in size to the drill bit 110 being utilized. The similar diameters of the drill bit 110 and a selectable bore 106 may allow the selectable bore 106 to guide and stabilize the drill bit 110 during use. Similarly, the fixed bore 104 may be of a similar diameter to the drill bit 110 providing further guidance and stability. Alternatively, the fixed bore 104 may be of a larger diameter than the drill bit 110 such that the drill bit 110 does not necessarily contact the walls of the fixed bore 104. An axle 109 may pass through a central bore 111 disposed within the bore selection member 108 about which the bore selection member 108 may rotate.

Figure 2:
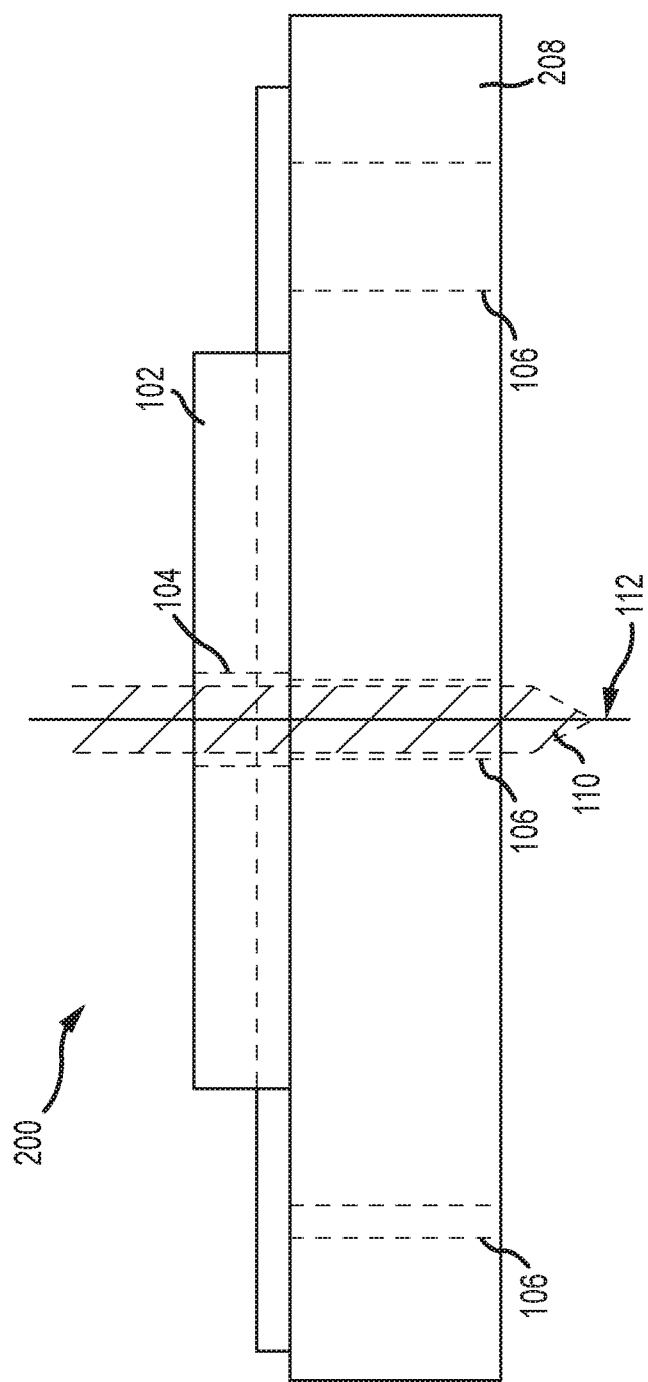
FIG. 2 is a schematic sectional view of an embodiment of a drill bit guide assembly featuring a sliding bore selection member.

Another embodiment of a drill bit guide assembly 200 is shown in FIG. 2. A guide member 102 includes at least a portion of a fixed bore 104. A bore selection member 208 may be slidably affixed to the drill bit guide assembly 200. The bore selection member 208 may include a plurality of selectable bores 106 which may be arranged linearly such that each may be aligned with the reference axis 112 allowing a drill bit 110 to pass through both the fixed bore 104 and a selectable bore 106. The bore selection member 208 may be attached in any well-known manner that provides relative movement between the bore selection member 208 and the guide member 102. One example is a tongue and groove in which one of the bore selection member 208 and the guide member 102 comprises a groove along one or more sides and in which a tongue is disposed upon the other of the bore selection member 208 or the guide member 102 in order to guide the bore selection member 208 as it is moved relative to the guide member 102.

Figure 3:
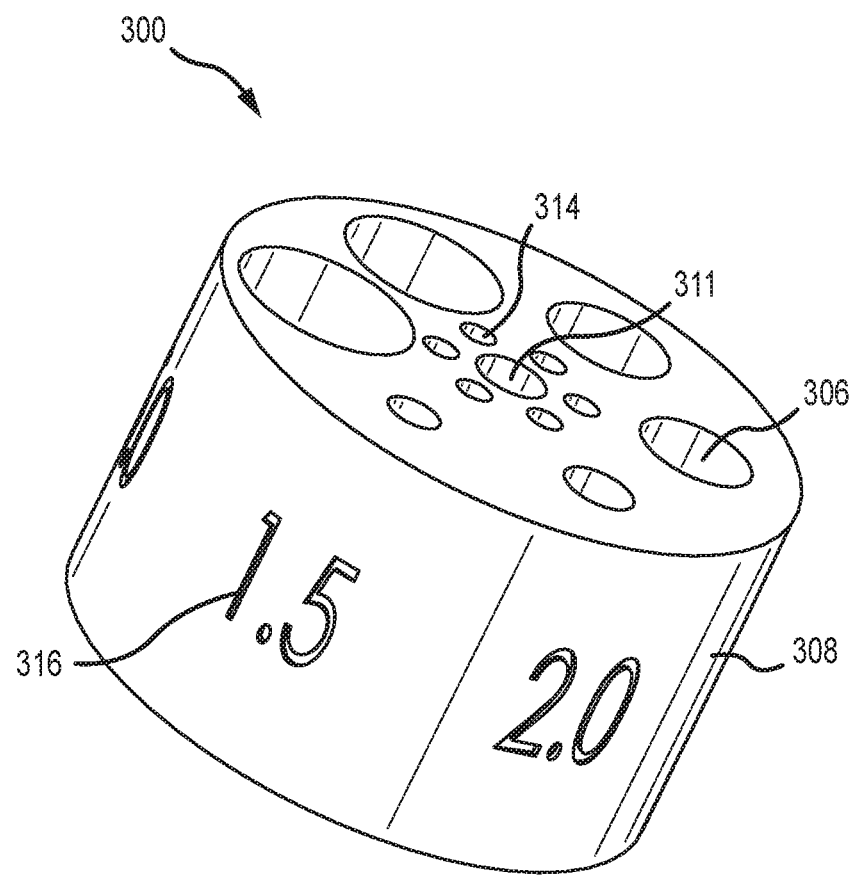
FIG. 3 is a perspective view of an embodiment of a rotational bore selection member.
Figure 4:
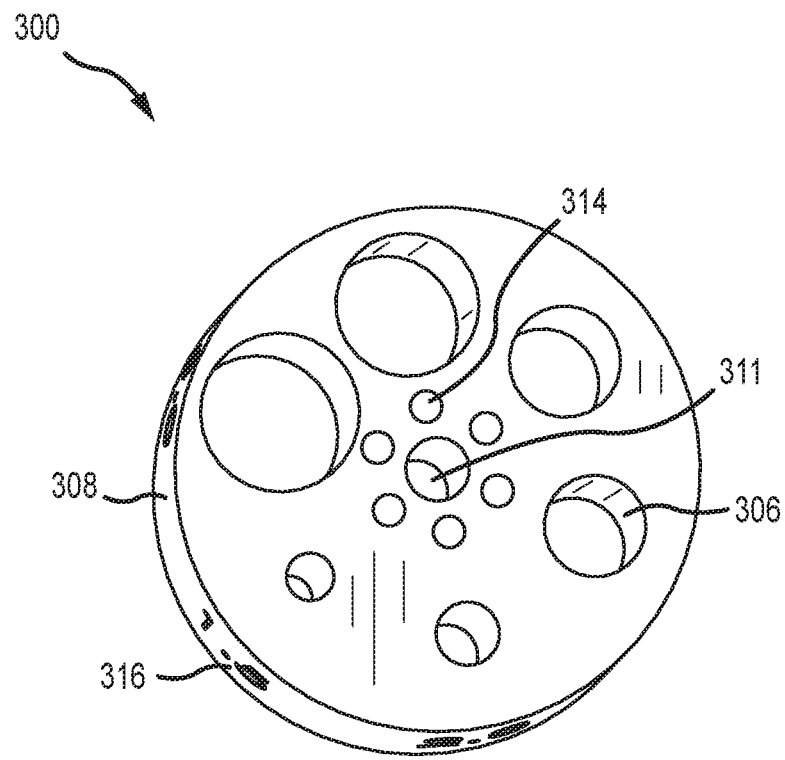
FIG. 4 is a perspective view an embodiment of a rotational bore selection member.

FIGS. 3-18 pertain to embodiments comprising a rotatable bore selection member similar to that of FIG. 1. FIGS. 3 & 4 depict an embodiment of a bore selection member 300 comprised of a plurality of selectable bores 306. The bore selection member 300 is further comprised of a plurality of locking cavities 314 which may be engageable with one or more locking pins to restrict movement of the bore selection member 300 relative to the drill bit guide assembly as will be discussed in greater detail below. A central bore 311 may be disposed near the center of the bore selection member 300 through which an axle may be disposed. Furthermore, a plurality of indicia 316 may be disposed upon a perimeter surface 308 of the bore selection member 300 to denote which selectable bore 306 is currently aligned with the fixed bore.

Figure 5:
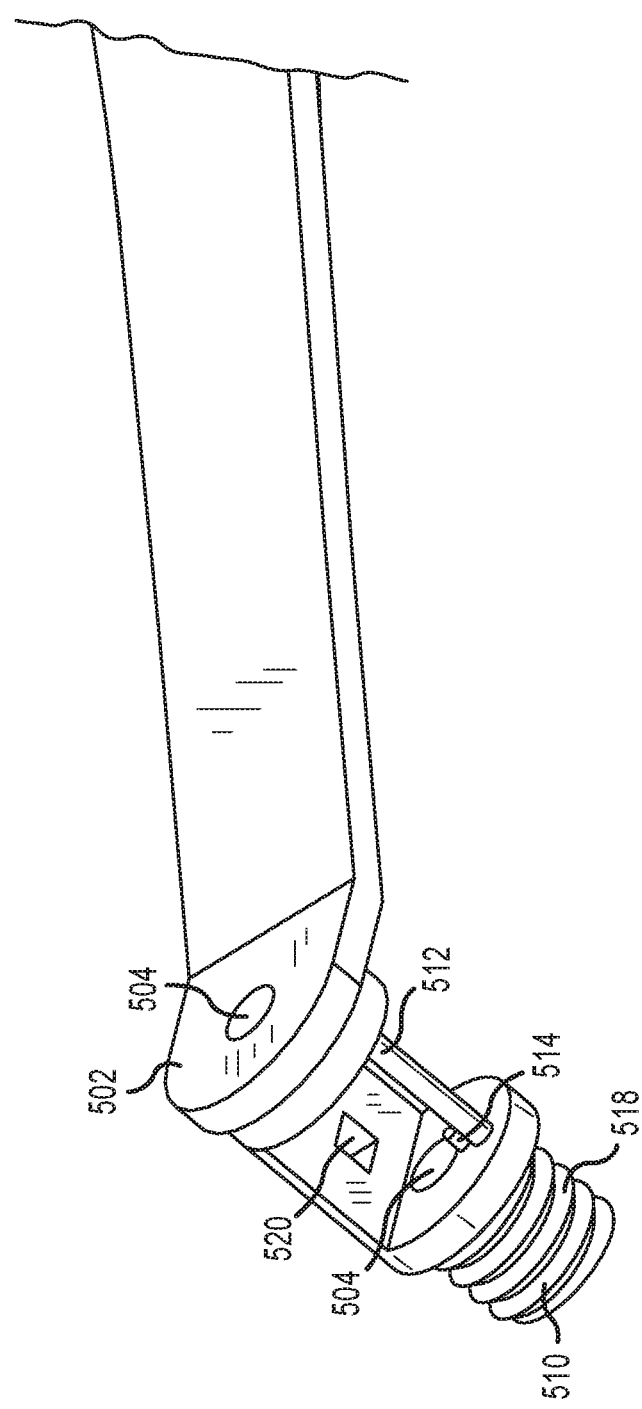
FIG. 5 is a perspective view of an embodiment of a drill bit guide assembly with a bore selection member removed for purposes of illustration to reveal a guide member with an axles, a locking pin, and an indicator comprising a viewing window.
Figure 6:
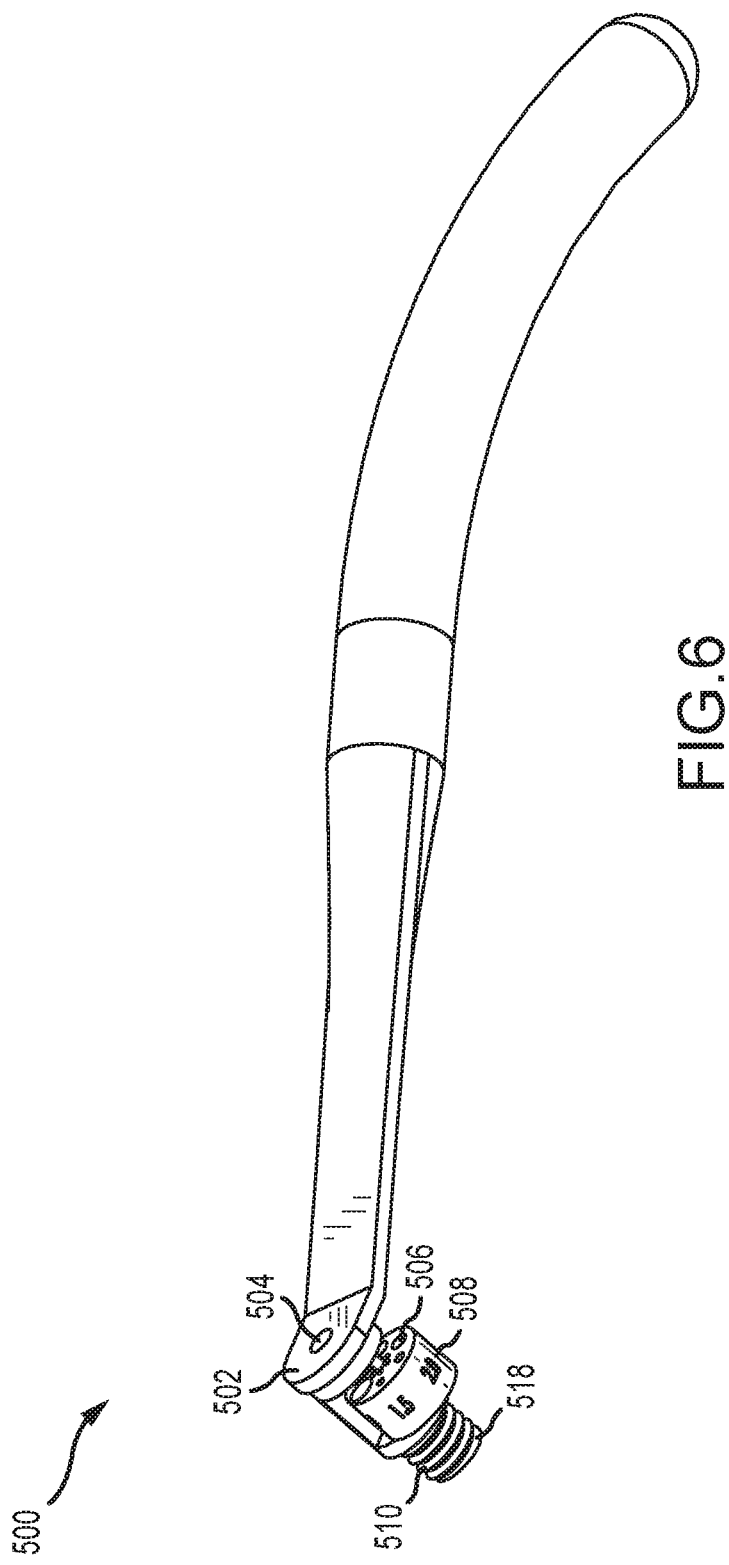
FIG. 6 is a perspective view of an embodiment of a drill bit guide assembly without an extension member, revealing an attaching mechanism comprising threads.
Figure 7:
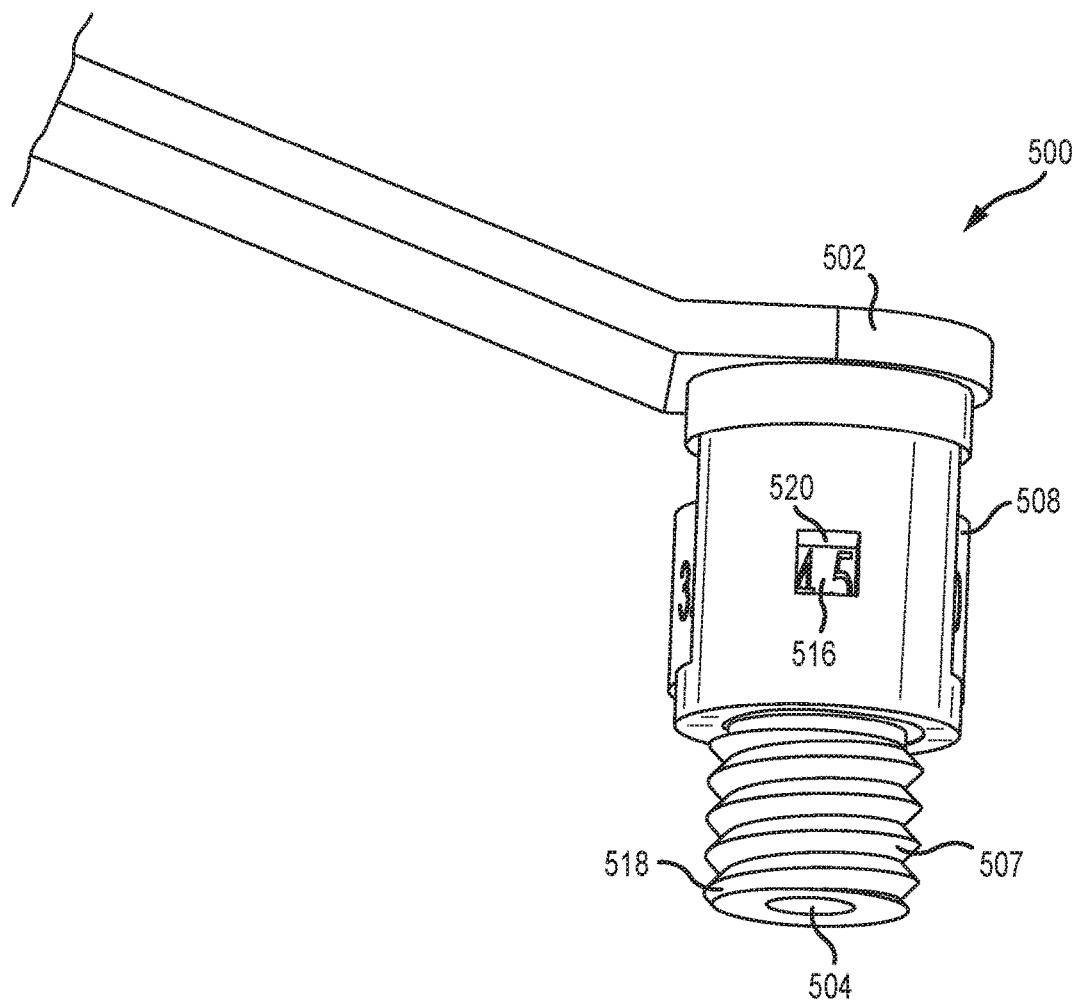
FIG. 7 is a perspective view of an embodiment of a drill bit guide assembly illustrating the denotation of the chosen selectable bore provided by the indicia of an indexing system.

FIGS. 5-7 illustrate an embodiment of a drill bit guide assembly 500. The guide member 502 comprises at least a portion of a fixed bore 504. The bore 504 may pass through a first and a second portion of the guide member 502 wherein the first and second portion are spaced apart by the bore selection member 508. An axle 512 is disposed upon the guide member 502 about which a bore selection member 508 may rotate. A locking pin 514 is disposed upon the guide member 500 which may engage a locking cavity (e.g., locking cavity 314 of FIG. 3) disposed upon a bore selection member 508 in order to index the selectable bores 506. In the embodiment shown, the locking pin 514 is disposed on a portion of the guide member 502 distal to the bore selection member 508. Importantly, the locking pin 514, or any other type of indexing member, may be disposed proximal to the bore selection member 508. Further, an indexing member may be disposed adjacent to the perimeter surface (e.g., perimeter surface 308 of FIG. 3) of the bore selection member 508 and engageable with a corresponding indexing member disposed upon the bore selection member 508. In any regard, a biasing member may be provided to retain a bore selection member 508 in a preferred location such that a user may manipulate a bore selection member 508 relative to an axle 512 to select a selectable bore 506. A biasing member may be a coiled spring, for example. In the illustrated example, an indicator comprised of a viewing window 520 may be disposed upon the guide member 500 to denote an indicium 516 disposed upon the bore selection member 508 correlating to the selectable bore 506 which is aligned with the fixed bore 504.

Figure 18:
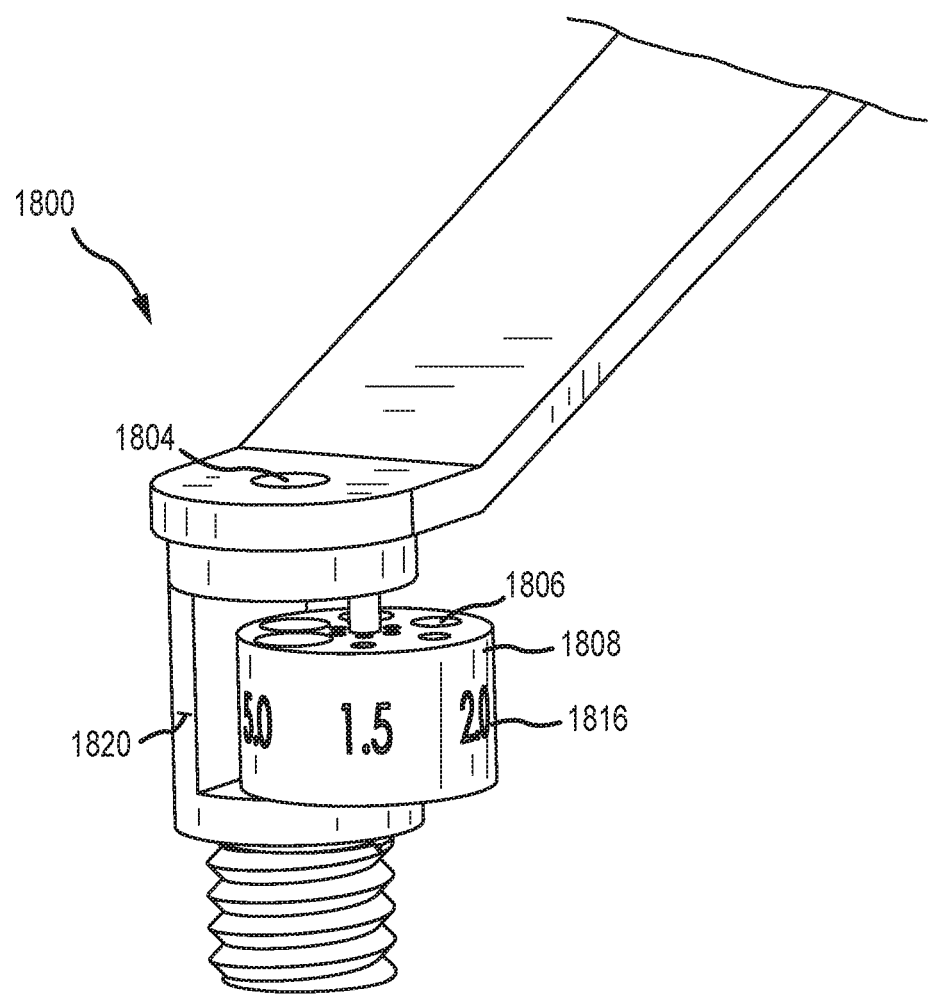
FIG. 18 is a perspective view of an embodiment of a drill big guide assembly.

With reference to FIG. 18, another embodiment of a drill bit guide assembly 1800 is shown that includes another manner in which a selected one of the selectable bores 1806 is indicated as being aligned with a fixed bore 1804. As above, the bore selection member 1808 may include indicia 1816 that may correspond with respective ones of the selectable bores 1806. In this regard, an indicator 1820 may be positioned adjacent to an indicium 1816 corresponding to the selectable bore 1806 aligned with the fixed bore 1804. This may provide an indication of the selectable bore 1806 that is aligned with the fixed bore 1804 that is provided by simply viewing the drill bit guide assembly 1800.

Figure 8:
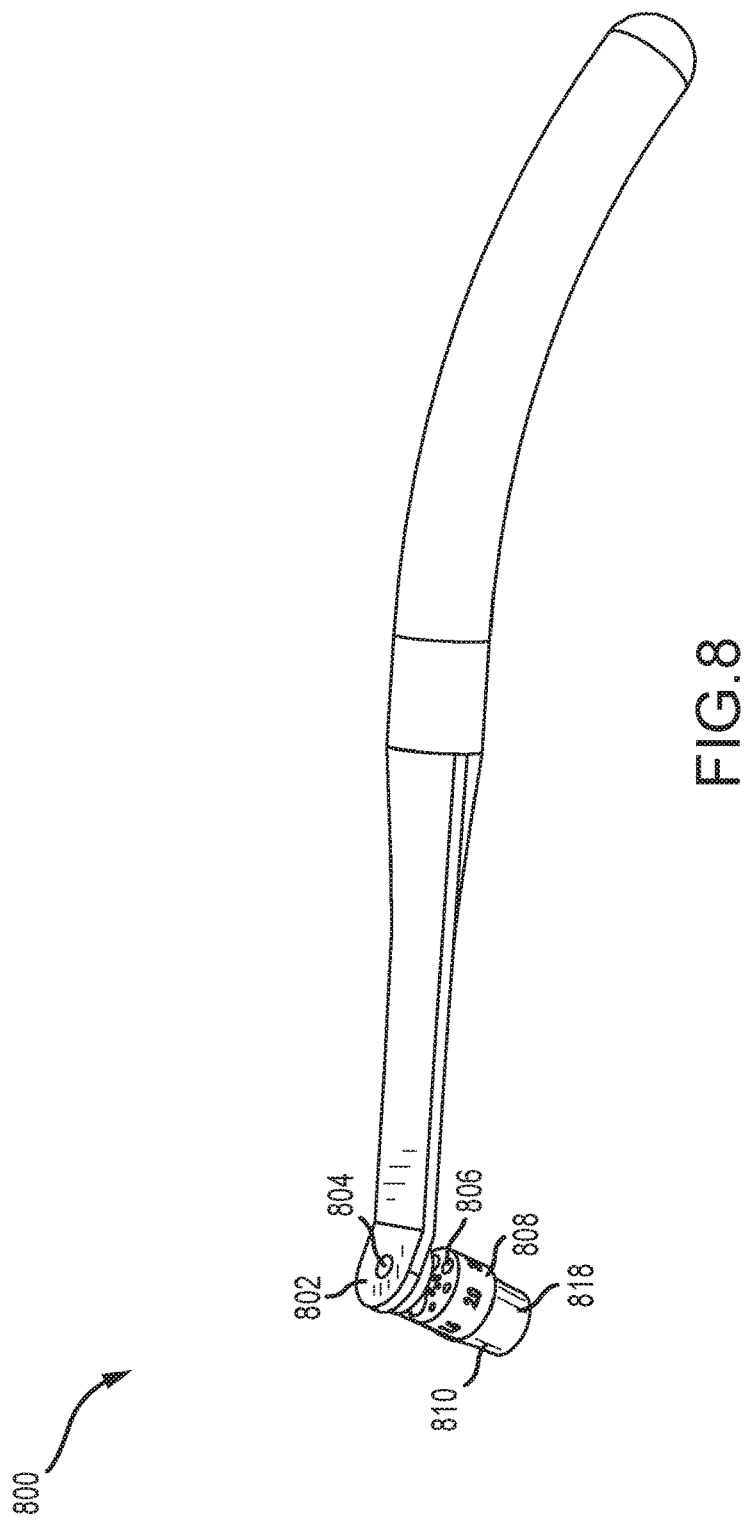
FIG. 8 is a perspective view of an embodiment of drill bit guide assembly with a single rotational bore selection member and an extension member.

FIG. 7 depicts an attaching mechanism comprised of threads 507 is disposed at a distal end 518 of the guide member 500 to receive a threaded extension member (e.g., extension member 810 of FIG. 8). The threads 507 allow extension members (e.g., extension member 810 of FIG. 8) of various size to be interchanged as needed during use. One of ordinary skill in the art will appreciate that different lengths and diameters may be preferred at different times without needing to change tools.

Figure 9:
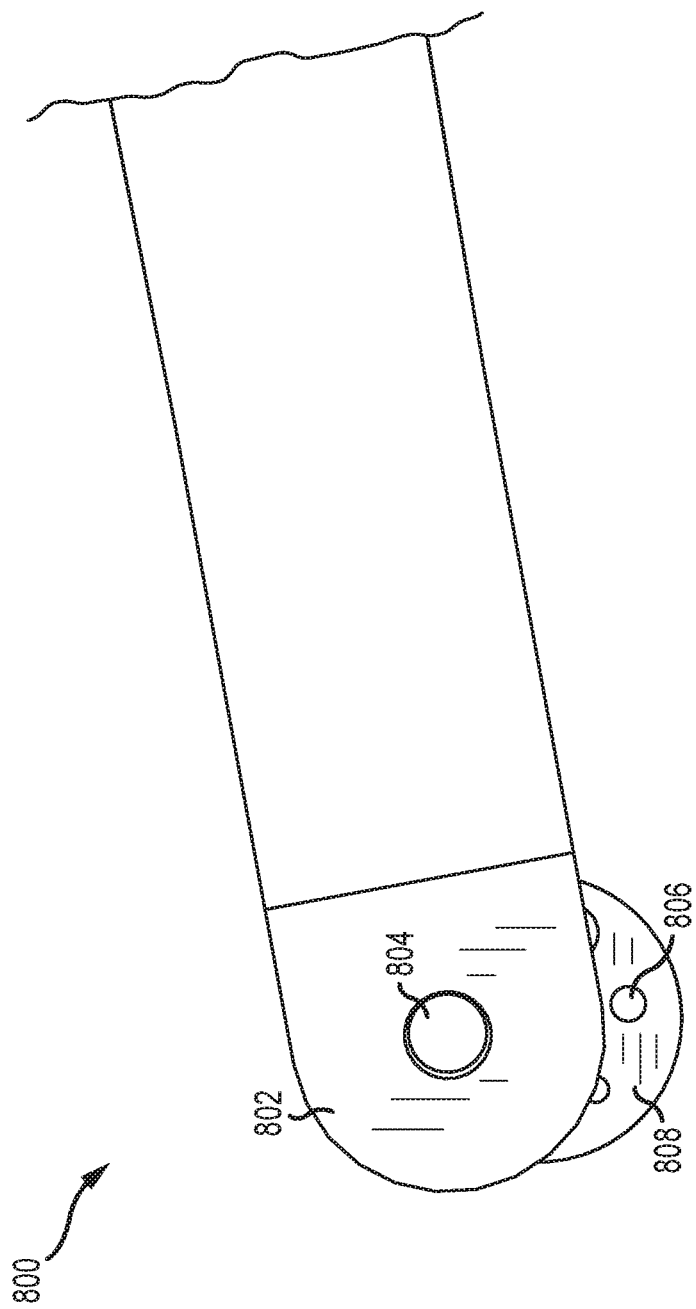
FIG. 9 is a perspective view of an embodiment of a drill bit guide assembly.

With reference to FIGS. 8-9, another embodiment of a drill bit guide assembly 800 is comprised of a guide member 802 which is comprised of at least a portion of a fixed bore 804. The drill bit guide assembly 800 is further comprised of a rotatable bore selection member 808. The bore selection member is comprised of a plurality of selectable bores 806. A distal end 818 of the drill bit guide assembly 800 may have an extension member 810 with a wide distal surface to rest externally against a patient's tissue. This may be in contrast to a narrow tip which may allow the distal end 818 to be inserted into an incision (e.g. extension member 1610 in FIGS. 16A & 16B). The extension members (e.g. 810 and 1610) may be interchangeable.

Figure 10:
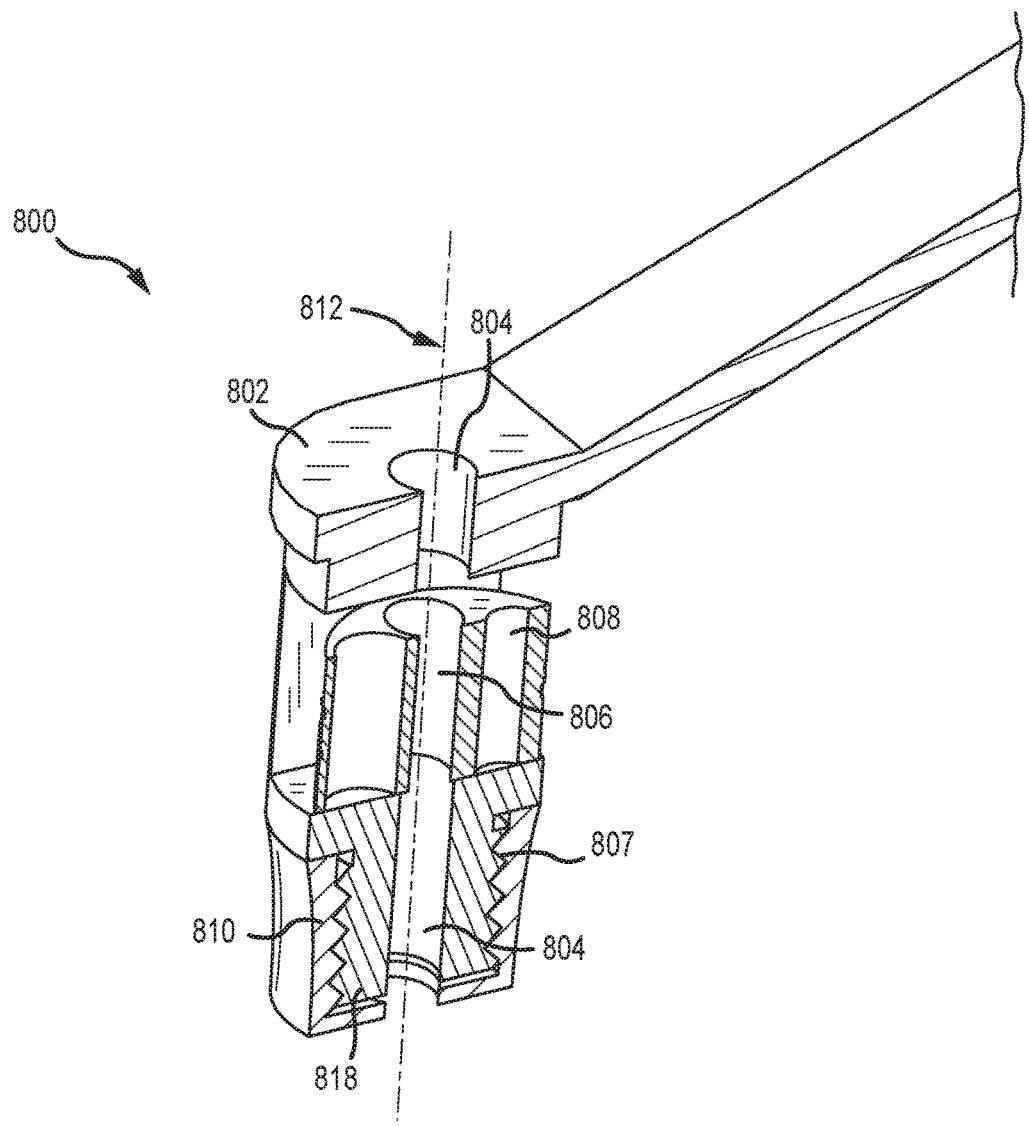
FIG. 10 is a cross sectional view of an embodiment of a drill bit guide assembly.

FIG. 10 is a cross sectional view of an embodiment of a drill bit guide assembly 800 similar to that of FIGS. 8 and 9. A guide member 802 may comprise at least a portion of a fixed bore 804 the central axis of which comprises a reference axis 812. The drill bit guide assembly 800 may be further comprised of a rotatable bore selection member 808 comprised of a plurality of selectable bores 806. A distal end 818 of the drill bit guide assembly 800 may be comprised of an attachment mechanism comprising threads 807 which are engageable to corresponding threads on an extension member 810. Alternatively, the attachment mechanism may be a friction or interference fitting, a clip and/or latch system, or any other well-known attaching device.

Figure 11:
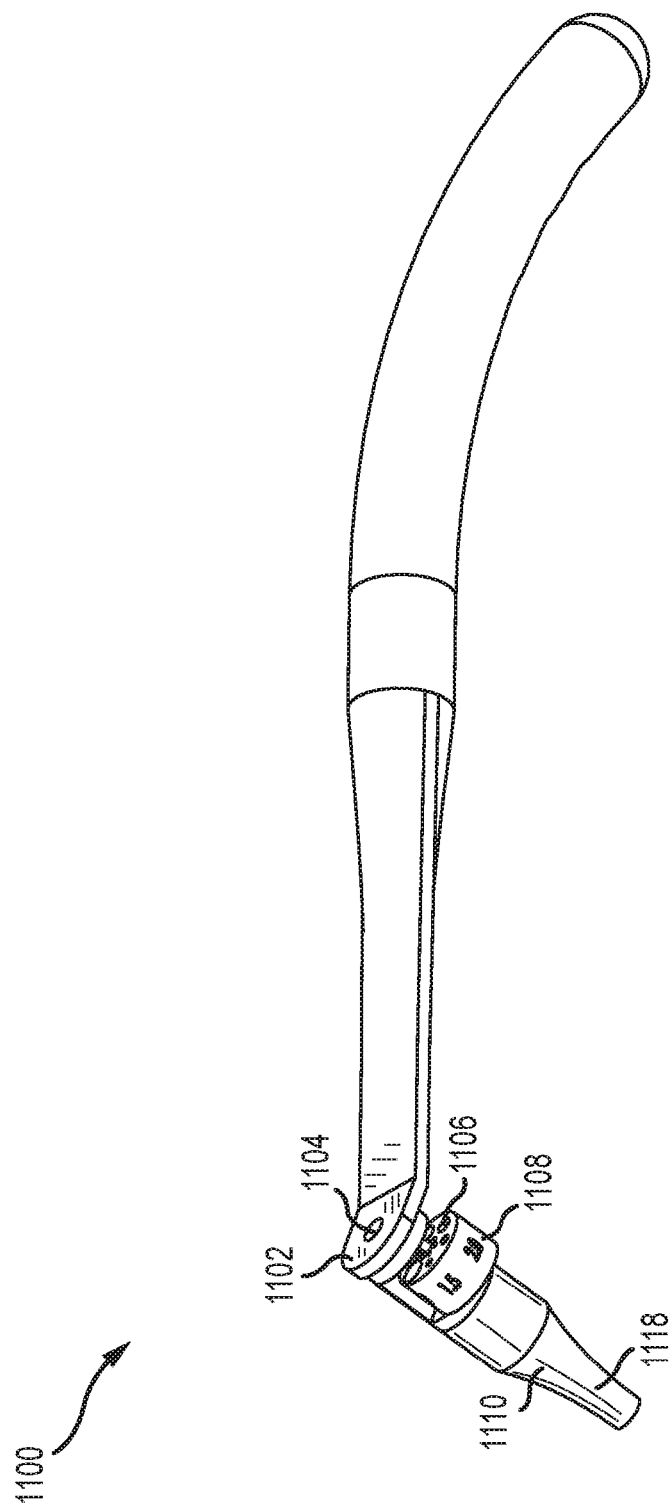
FIG. 11 is a perspective view of an embodiment of a drill bit guide assembly with a single rotational bore selection member and an extension member.

In another embodiment of a drill bit guide assembly 1100 shown in FIG. 11, a distal end 1118 may be elongated to provide improved stability to the drill bit. The elongated portion which comprises at least a portion of a fixed bore 1104 may be a portion of the guide member 1102 itself or may be an attachable extension member 1110. In this embodiment the guide member 1102 houses at least a portion of the fixed bore 1104 and a bore selection member 1108. The bore selection member is comprised of a plurality of selectable bores 1106.

Figure 12:
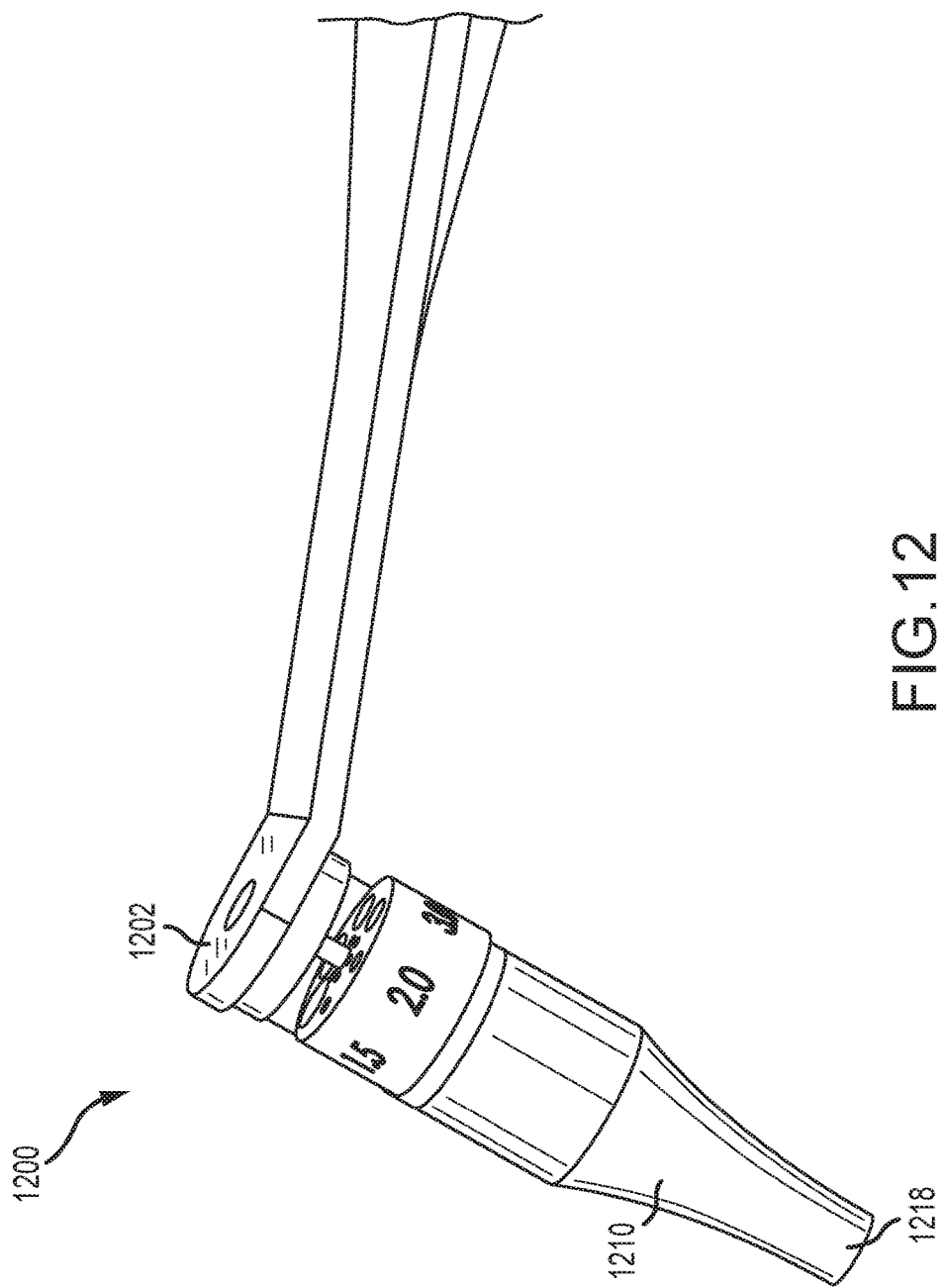
FIG. 12 is a perspective view of an embodiment of a drill bit guide assembly with a single rotational bore selection member and an extension member.

In an embodiment of a drill bit guide assembly 1200 shown in FIG. 12, an elongated extension member 1210 may be disposed upon a distal end 1218 of the drill bit guide assembly. The extension member 1210 may be attachable to the guide member 1202 with an attaching mechanism comprised of threads which are concealed and not visible in FIG. 12. Different lengths and diameters may be preferred for different tasks and the interchangeability of extension members 1210 may allow for expedient adaptation of the assembly.

Figure 13:
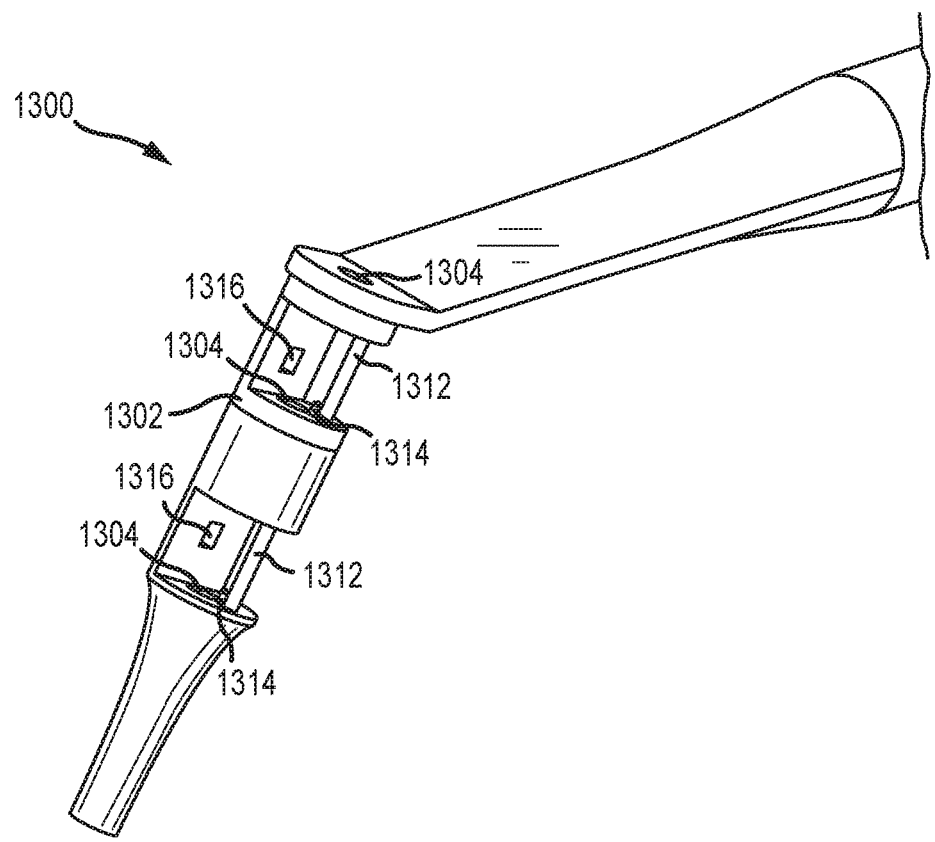
FIG. 13 is a perspective view of an embodiment of a guide member capable of housing two rotational bore selection members.
Figure 14:
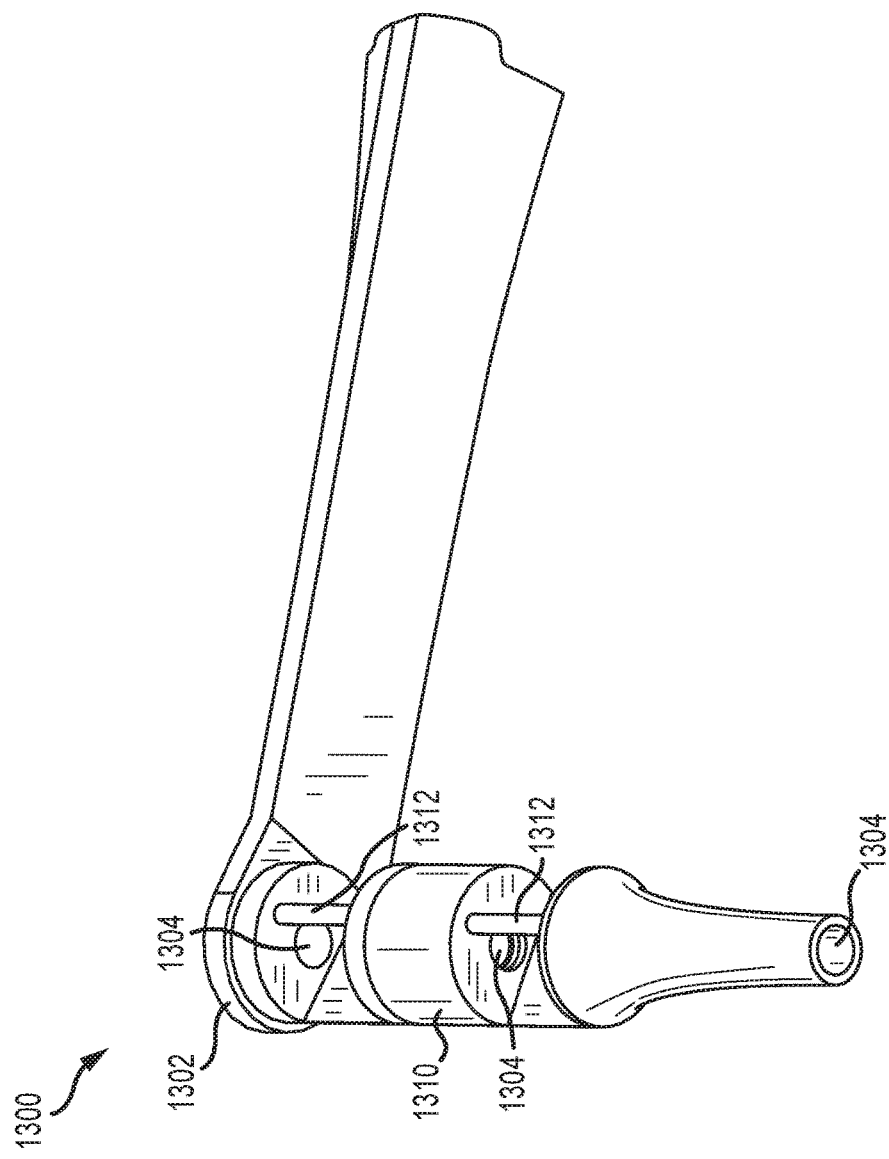
FIG. 14 is a perspective view of an embodiment of a guide member.
Figure 15:
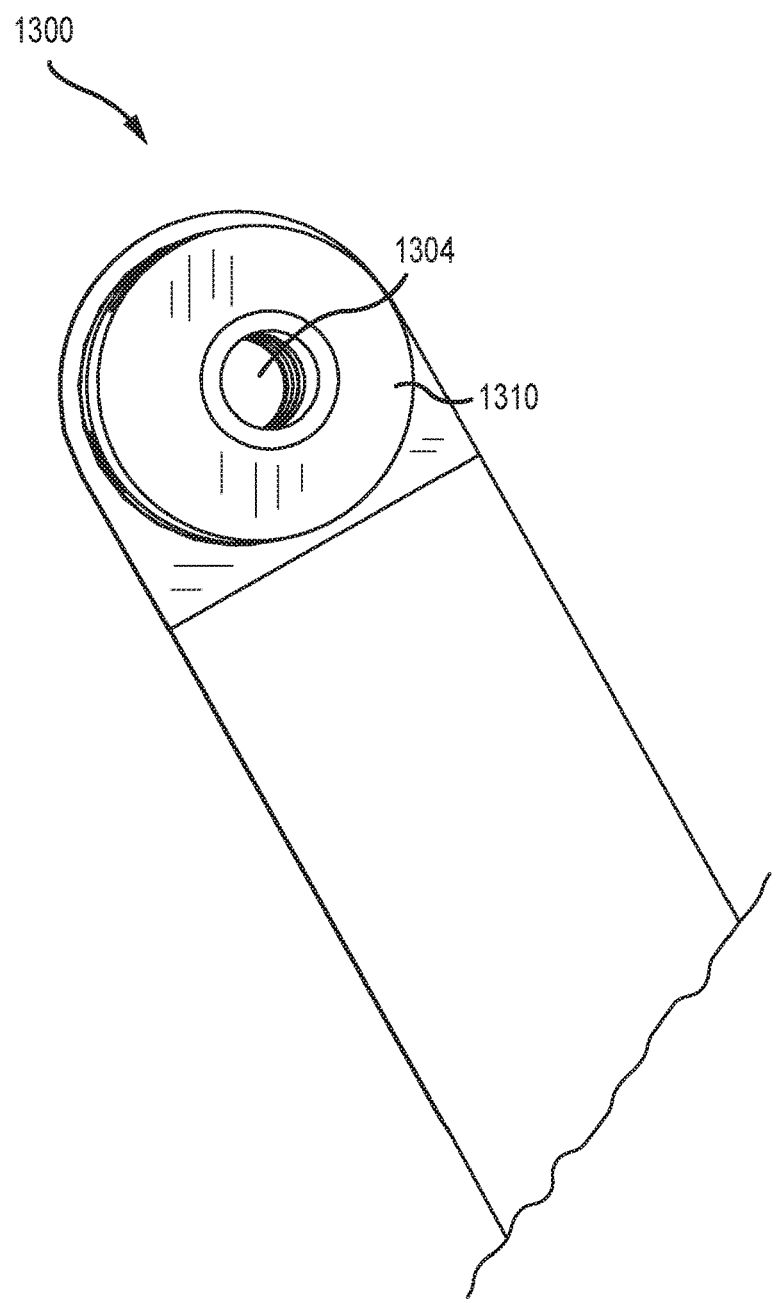
FIG. 15 is a perspective view of an embodiment of a drill bit guide assembly.
Figure 16A:
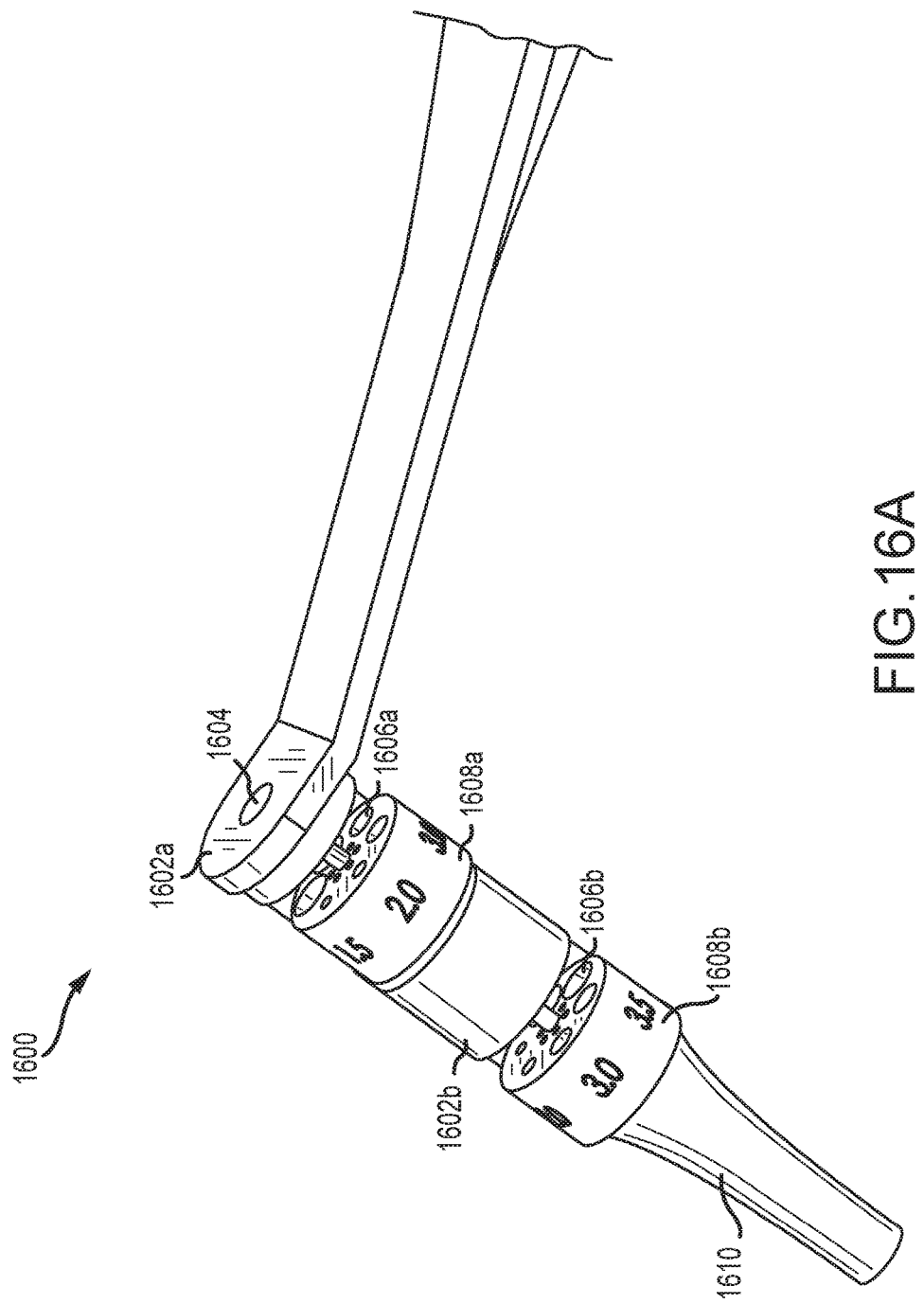
FIGS. 16A & 16B are perspective views of an embodiment of a drill bit guide assembly featuring two rotatable bore selection members with different respective handle configurations.
Figure 16B:
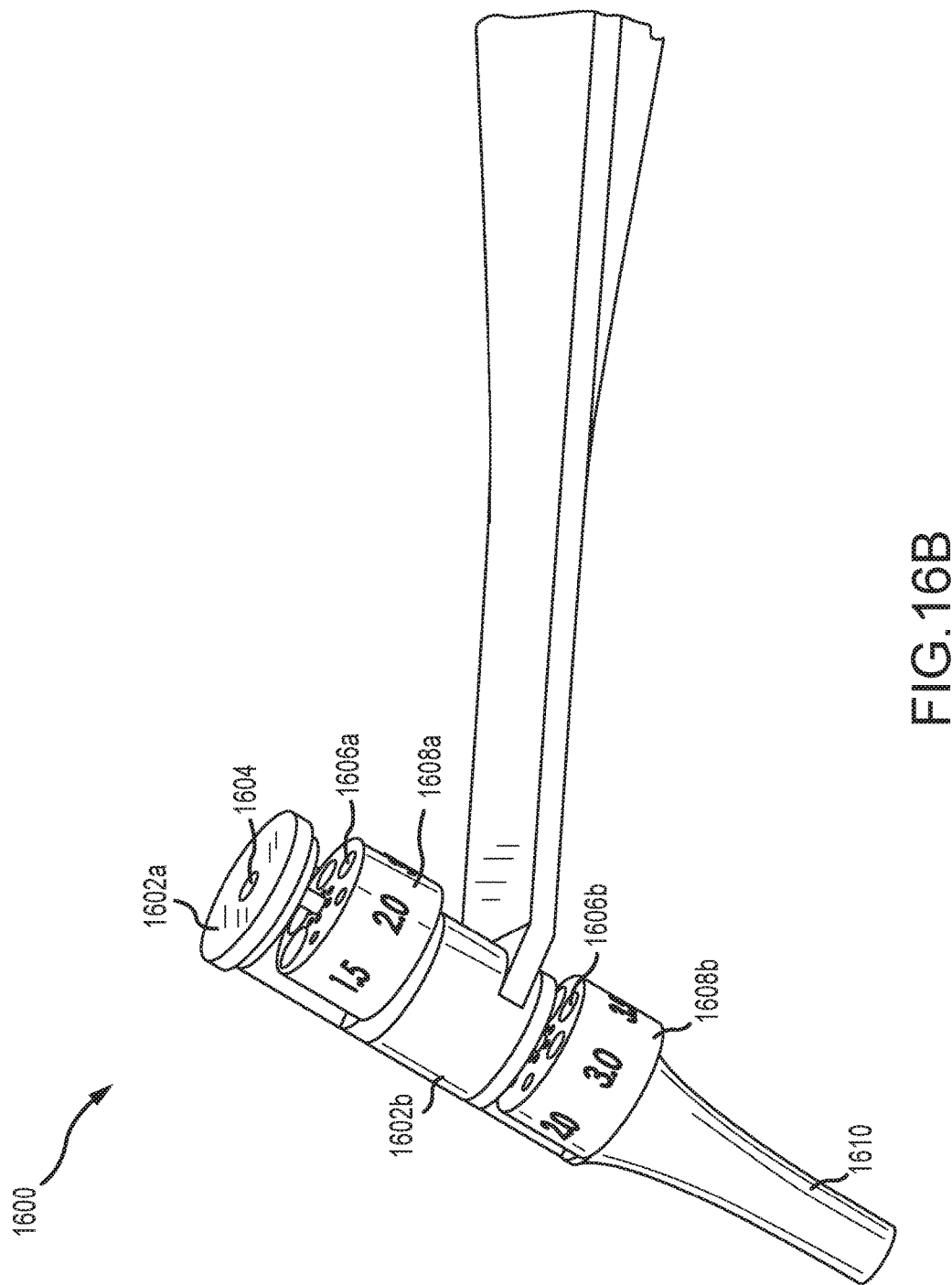

FIGS. 13-15 illustrate an embodiment of a guide member 1300 with the bore selection members removed for illustrative purposes. A guide member 1300 may comprise at least a portion of a fixed bore 1304. An indicator comprised of a viewing window 1316 may be disposed upon the guide member 1300. The guide member 1300 may further comprise an axle 1312 about which a bore selection member (e.g. bore selection member 308 of FIG. 3) may be disposed. A locking pin 1314 may be disposed upon the guide member 1302 to lockably engage a locking bore on a bore selection member. An extension member 1310 may be attachable to the guide member 1302 or may alternately be permanently attached or monolithic with the guide member 1302.

Figure 17:
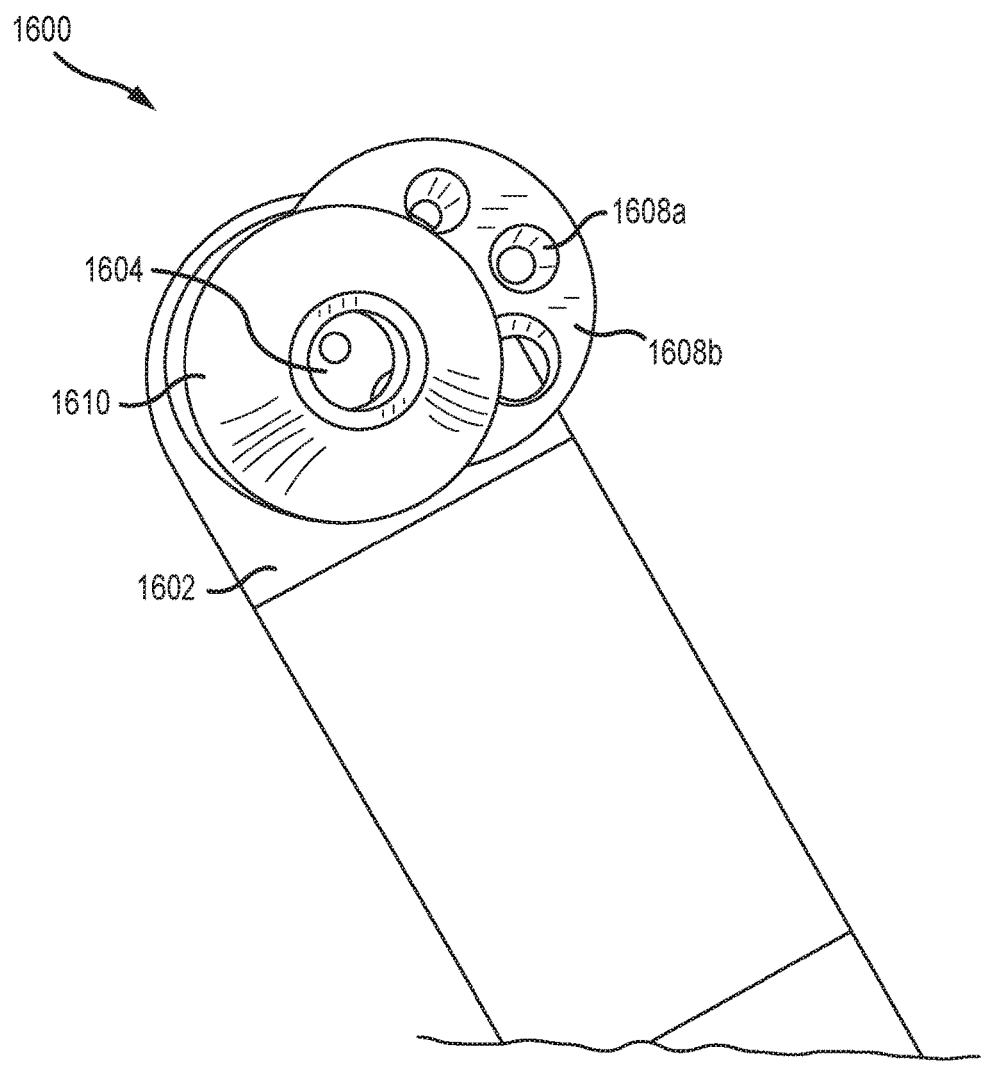
FIG. 17 is a perspective view of an embodiment of a drill bit guide assembly with two bore selection members.

A drill bit guide assembly 1600 that includes two rotatable bore selection members 1608 is shown in FIGS. 16-17. The bore selection members 1608 are disposed about axles (e.g. axles 1312 in FIG. 13) allowing a selectable bore 1606 to be aligned with the fixed bore 1604 and the reference axis 1612. An upper bore selection member 1608a may include selectable bores 1606 with similar or equal diameters to the selectable bores 1606 of a lower bore selection member 1608b. In this scenario, if a drill bit (e.g., drill bit 110 in FIG. 1) with a small diameter relative to fixed bore 1604 were used, each of the bore selection members 1608 may be positioned such that a selectable bore 1606 on each bore selection member 1608 of similar diameter to the drill bit may be used to guide the drill bit. Furthermore, in such a scenario, the drill bit may contact the walls of the selectable bores 1606 and may or may not contact the walls of the fixed bore 1604.

In another embodiment of a drill bit guide assembly 1600 the diameters of the selectable bores 1606 of the lower bore selection member 1608b may be different than those of the upper bore selection member 1608a. For example, the diameters of the selectable bores 1606 of the lower bore selection member 1608b may be smaller than the selectable bores 1606 of the upper bore selection member 1608a. This scenario would allow a relatively small drill bit to pass freely through a selectable bore 1606 of the upper bore selection member 1608a and engage a selectable bore 1606 of similar diameter to the drill bit in the lower bore selection member 1608b. Accordingly, each selectable bore 1606 may be sized such that its diameter is different than each other selectable bore 1606. Such an embodiment may allow a greater variety of selectable bore 1606 diameters to be disposed upon the drill bit guide assembly 1600 than if the plurality of bore selection members 1608 housed selectable bores 1606 of similar diameters to the other bore selection members 1608. Accordingly, the drill bit guide assembly 1600 may function with a greater variety of drill bit diameters and reduce clutter and confusion which may be caused by the necessity for multiple traditional drill bit guides. A detachable extension member 1610 may comprise a lower guide member 1602b and lower bore selection member 1608b. Alternately, the lower guide member 1602b may be permanently attached or monolithic with the upper guide member 1602a.

Those skilled in the art will appreciate that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. A drill bit guide assembly for use with a drill, comprising:
  a fixed bore adapted for receipt of a drill bit during use of the drill bit, the fixed bore extending through at least a portion of a guide member, wherein a central axis of the fixed bore comprises a reference axis;
  a plurality of selectable bores each having a different diameter;
  a bore selection member comprising at least one of the plurality of selectable bores, the bore selection member being displaceable relative to the fixed bore for aligning at least one of the selectable bores with the reference axis; and a bore extension member, wherein a distal end of the guide member comprises an attaching mechanism which is engageable to the bore extension member, wherein the fixed bore extends through the bore extension member when the bore extension member is engaged with the guide member, and wherein the attaching mechanism comprises threads, and the bore extension member comprises complementary threads for securing the bore extension member to the guide member.

2. The drill bit guide assembly of claim 1, wherein the bore extension member is selectable from a plurality of bore extension members.

3. The drill bit guide assembly of claim 2, wherein a second bore extension member of the plurality of bore extension members has a length that is different than a length of the bore extension member.

4. The drill bit guide assembly according to claim 1, wherein the bore selection member is affixed to the guide member for movement relative to the fixed bore.

5. The drill bit guide assembly according to claim 4, wherein the bore selection member comprises the plurality of selectable bores.

6. The drill bit guide assembly according to claim 5, wherein the bore selection member is rotatable relative to the fixed bore.

7. The drill bit guide assembly according to claim 6, wherein the bore selection member is comprised of a distal surface and a proximal surface and a perimeter surface extending between the distal surface and the proximal surface, wherein the bore selection member is disposed about an axle affixed to the guide member and the bore selection member is rotatable about the axle, wherein the axle extends parallel to and is eccentrically disposed from the reference axis and the plurality of selectable bores each extend parallel to the reference axis from the proximal surface to the distal surface of the bore selection member.

8. The drill bit guide assembly according to claim 7, further comprising an index system comprising a first indexing member fixedly disposed relative to the fixed bore and a second indexing member fixedly disposed relative to the bore selection member, wherein the first indexing member and the second indexing member cooperate to align at least one of the plurality of selectable bores with the fixed bore.

9. The drill bit guide assembly according to claim 8, wherein the first indexing member is comprised of a locking pin and the second indexing member is comprised of at least one locking cavity, wherein the bore selection member is movable longitudinally along the axle allowing the locking pin to engage a locking cavity and restrict rotation of the bore selection member relative to the reference axis.

10. The drill bit guide assembly according to claim 9, wherein the index system is further comprised of a plurality of indicia and the indicia are disposed relative to the plurality of selectable bores, wherein the indicia denote a size of the at least one selectable bore aligned with the fixed bore.

11. The drill bit guide assembly according to claim 10, further comprising an indicator fixedly disposed to the guide member, wherein the indicator is alignable with the indicia to denote the at least one selectable bore aligned with the fixed bore.

12. The drill bit guide assembly according to claim 6, further comprising a second bore selection member comprising at least one of a second plurality of selectable bores, the second bore selection member being displaceable relative to the fixed bore for aligning at least one of the second plurality of selectable bores with the reference axis.

13. The drill bit guide assembly according to claim 5, wherein the bore selection member is linearly slidable relative to the fixed bore.

14. The drill bit guide assembly according to claim 13, further comprising a second bore selection member comprising at least one of a second plurality of selectable bores, the second bore selection member being displaceable relative to the fixed bore for aligning at least one of the second plurality of selectable bores with the reference axis.

15. The drill bit guide assembly according to claim 13, further comprising an index system comprising a first indexing member fixedly disposed relative to the fixed bore and a second indexing member fixedly disposed relative to the bore selection member, wherein the first indexing member and the second indexing member cooperate to align at least one of the plurality of selectable bores with the fixed bore.

16. The drill bit guide assembly according to claim 15, wherein the first indexing member is comprised of a locking pin and the second indexing member is comprised of at least one locking cavity, wherein the bore selection member is movable longitudinally to allow the locking pin to engage a locking cavity and restrict movement of the bore selection member relative to the reference axis.

17. The drill bit guide assembly according to claim 16, wherein the index system is further comprised of a plurality of indicia and the indicia are disposed relative to the plurality of selectable bores, wherein the indicia denote the at least one selectable bore aligned with the fixed bore.

18. The drill bit guide assembly according to claim 17, further comprising an indicator fixedly disposed to the guide member, wherein the indicator is alignable with the indicia to denote the at least one selectable bore aligned with the reference axis.

* * * * *